United States Patent [19]

Pentoney, Jr. et al.

[11] Patent Number: 5,630,925
[45] Date of Patent: May 20, 1997

[54] CAPILLARY ELECTROPHORESIS USING A CONDUCTIVE CAPILLARY TUBE

[75] Inventors: Stephen L. Pentoney, Jr., Yorba Linda; Kenneth D. Konrad, Long Beach, both of Calif.

[73] Assignee: Beckman Instruments, Inc., Fullerton, Calif.

[21] Appl. No.: 501,836

[22] Filed: Jul. 13, 1995

[51] Int. Cl.⁶ .................................................... G01N 27/26
[52] U.S. Cl. .......................... 204/604; 204/433; 204/601; 204/451
[58] Field of Search ........................... 204/299 R, 180.1, 204/604, 453

[56] References Cited

U.S. PATENT DOCUMENTS 4,842,701   6/1989   Smith et al. .......................... 204/180.1

OTHER PUBLICATIONS

"Postcolumn Radionuclide Detection of Low-Energy β Emitters in Capillary Electrophoresis," by Tracht et al., Anal. Chem., 1994, 66, 2382–2389.

Primary Examiner—Kathryn L. Gorgos
Assistant Examiner—Alex Noguerola
Attorney, Agent, or Firm—William H. May; Janis C. Henry

[57] ABSTRACT

An electrophoretic system employing a capillary with at least one end having an electrically conductive coating or layer directly thereon. In order to introduce a plug of sample from a small amount of the sample in a vial, the conductive tip is submersed into the small amount of sample and an electric field is applied at the end by applying the high voltage to the tip in order to electrokinetically inject a plug of the sample. The conductive tip may also be used as a terminal for completing the circuit for applying the high voltage across the capillary column for electrophoresis. The separated components may be collected on a surface or small amount of buffer to reduce sample dilution or mixing of one sample component with a different sample component from the electrophoretic process.

8 Claims, 3 Drawing Sheets

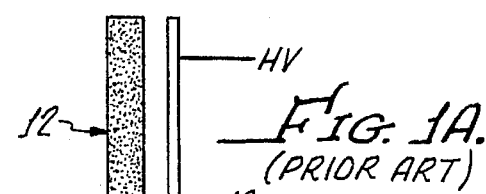
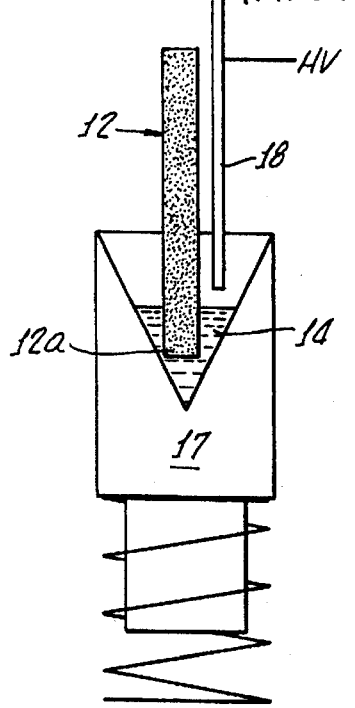
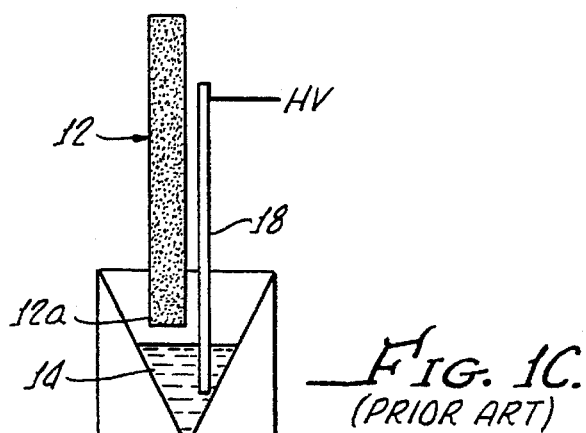
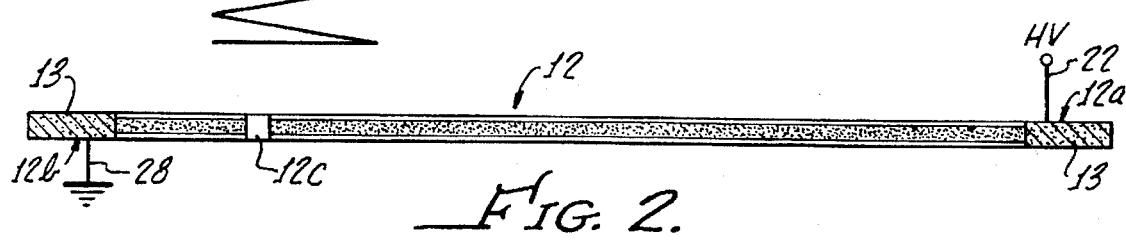

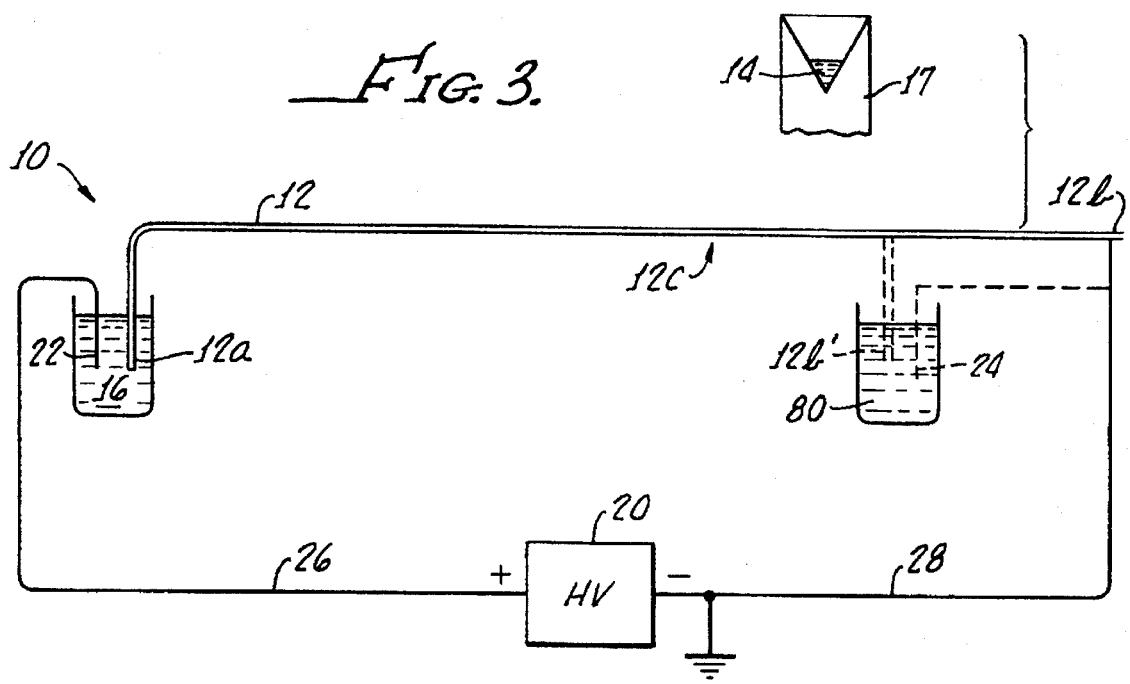
Fig. 3.
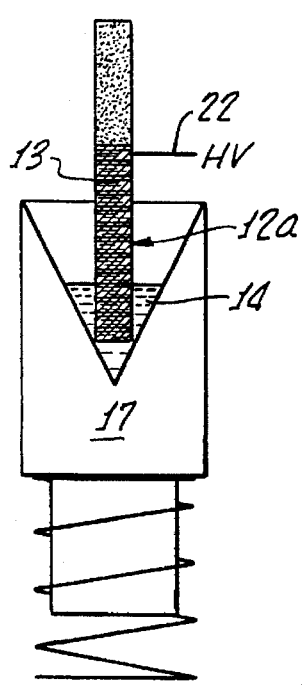
Fig. 4.
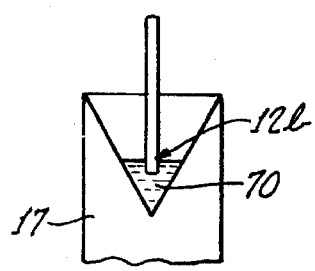
Fig. 5.
Fig. 6.

CAPILLARY ELECTROPHORESIS USING A CONDUCTIVE CAPILLARY TUBE

BACKGROUND OF THE INVENTION

This invention relates to electrophoresis in general and, in particular, to an electrophoretic system employing a capillary with a conductive tip.

Capillary electrophoresis (CE) in narrow channels has proven useful as an efficient method for the separation of samples. An electric field is applied in the channel containing an electrolyte and a sample. The electric field causes the sample to separate its components which can be detected and collected if desired. CE is advantageous because it requires only very small sample volumes, such as the contents of a cell or similar subcompartments.

In the electrophoresis process, a high voltage on the order of several tens of thousands of volts is applied between the inlet and the outlet of a capillary channel in order to cause the sample to migrate and separate in a reasonable time and with reasonable resolution. In some conventional electrophoretic schemes, a capillary tube is employed having an inlet end and an outlet end. The tube is filled with an electrolyte such as a liquid buffer or a gel and a sample is introduced into the inlet end. Both the inlet and outlet ends are then immersed into buffer solutions and a high voltage is applied between the two buffer solutions in order to cause a high electric field in the capillary tube.

It is frequently desirable to make reliable electric contact between an electrolyte-filled capillary separation channel and a minimum amount of electrolyte contained in an inlet or outlet electrolyte buffer reservoir. A particular problem is encountered in electrokinetic sample injection where only a small volume of sample solution is available for injection. This is illustrated in reference to FIGS. 1A–1C below.

In electrokinetic injection, the inlet end 2a of a capillary 2 is immersed in a sample 14 and an electrical potential is applied across the electrolyte in the capillary so as to draw a portion of the sample 14 into the inlet end 2a. In order to apply an electrical potential between the two ends of the capillary, an electrode 18 is also submerged into the sample 14 in the configuration shown in FIG. 1A. The sample 14 is contained in the container 17. In actual operation, end 2a and electrode 18 are placed side by side and the container 17 may be moved upwards until both end 2a and the tip of electrode 18 are submerged in sample 14. Then an electrical potential is applied across the ends of the capillary using electrode 18 in order to inject a plug of sample into the inlet end 2a.

The above-described design and operation work very well for sample volumes greater than a few microliters but becomes less reliable as the sample volume is reduced. The problem which arises as the sample volume becomes increasingly small is depicted in FIGS. 1B, 1C. As illustrated in these two figures, any misalignment between the electrode 18 and the capillary 2 can cause the injection mechanism for the sample to fail. In FIG. 1B, for example, the electrode 18 does not extend as far downward as the capillary inlet end 2a. In this case, only the inlet 2a is submerged in the sample solution during the attempted injection process. The process in this case would fail since electrode 18 would fail to assist in applying an electrical potential across the ends of the capillary. In FIG. 1C, the capillary end 2a does not reach the sample solution 14 even though the tip of electrode 18 does reach the sample solution. Therefore, the sample injection would again fail.

In addition to sample injection, there may be applications where it is desirable to make reliable electrical contact between an electrolyte-filled separation channel and a small amount of electrolyte contained in an inlet or outlet electrolyte medium such as a reservoir. It is therefore desirable to provide an improved electrophoretic system in which the above-described difficulties are avoided.

SUMMARY OF THE INVENTION

This invention is based on the observation that the above-described problem in sample injection can be altogether avoided if the tip of the capillary is made electrically conductive, so that the misalignment problem illustrated above in FIGS. 1B, 1C would be eliminated. Furthermore, the conductive capillary tube can also be used during electrophoresis to enable the collection of separated sample components in their separated state and to reduce the dilution of such components in buffer.

One aspect of the invention is directed towards an apparatus for electrophoretic separation of a sample, comprising a capillary having an end, said capillary containing a sample, an electrically conductive terminal attached to the tube at said end, and means for applying an electric field across the length of a section of the tube, said applying means electrically connected to said terminal to apply said electric field in order to separate the sample in the capillary into its components.

Another aspect of the invention is directed towards an apparatus for electrokinetic injection of a sample, comprising a capillary tube having an end, an electrically conductive terminal attached to the tube at said end, and means electrically connected to said terminal for applying an electric field at said end of the tube so that when said end is submersed in the sample, the electric field present at said end will cause a portion of said sample to be introduced into the tube.

Another aspect of the invention is directed towards a method for electrokinetic injection of a sample. The method comprises the steps of providing a capillary tube having an end and an electrically conductive terminal attached to the tube at said end, submersing said end and terminal in a sample, and applying an electric field at said end of the tube by means of said terminal, so that the electric field present at said end will cause a portion of said sample to be introduced into the tube through said end.

Yet another aspect of the invention is directed towards a method for electrophoretic separation of a sample, comprising the steps of providing the capillary tube having an end, said tube containing a sample, said tube having an electrically conductive terminal attached to it at said end, and electrically connecting a power supply to said terminal to apply an electric field across the length of a section of the tube in order to separate said sample into its components.

BRIEF DESCRIPTION OF THE DRAWINGS

FIG. 1A is a partly side view and partly cross-sectional view of a vial containing a sample solution and of sections of the capillary and an electrode to illustrate a conventional method of sample injection.

FIGS. 1B, 1C are partly side view and partly cross-sectional view of the vial, capillary and electrode of FIG. 1A, but where the capillary and electrode are misaligned to illustrate the problems of conventional sample injection.

FIG. 2 is a side view of a capillary with a metallized tip to illustrate the preferred embodiment of the invention.

FIG. 3 is a schematic view of an electrophoretic system to illustrate the preferred embodiment of the invention.

FIG. 4 is a partly cross-sectional and partly side view of a vial containing a sample and of a section of the capillary of FIGS. 2 and 3 to illustrate the preferred embodiment of the invention when used for sample injection.

FIG. 5 is a schematic view of a portion of an electrophoretic system to illustrate another aspect of the invention.

FIG. 6 is a schematic view of a portion of an electrophoretic system to illustrate yet another aspect of the invention.

For simplicity in description, identical components are labeled with the same numerals in the figures of this application.

DETAILED DESCRIPTION OF THE PREFERRED EMBODIMENT

Figure 7:
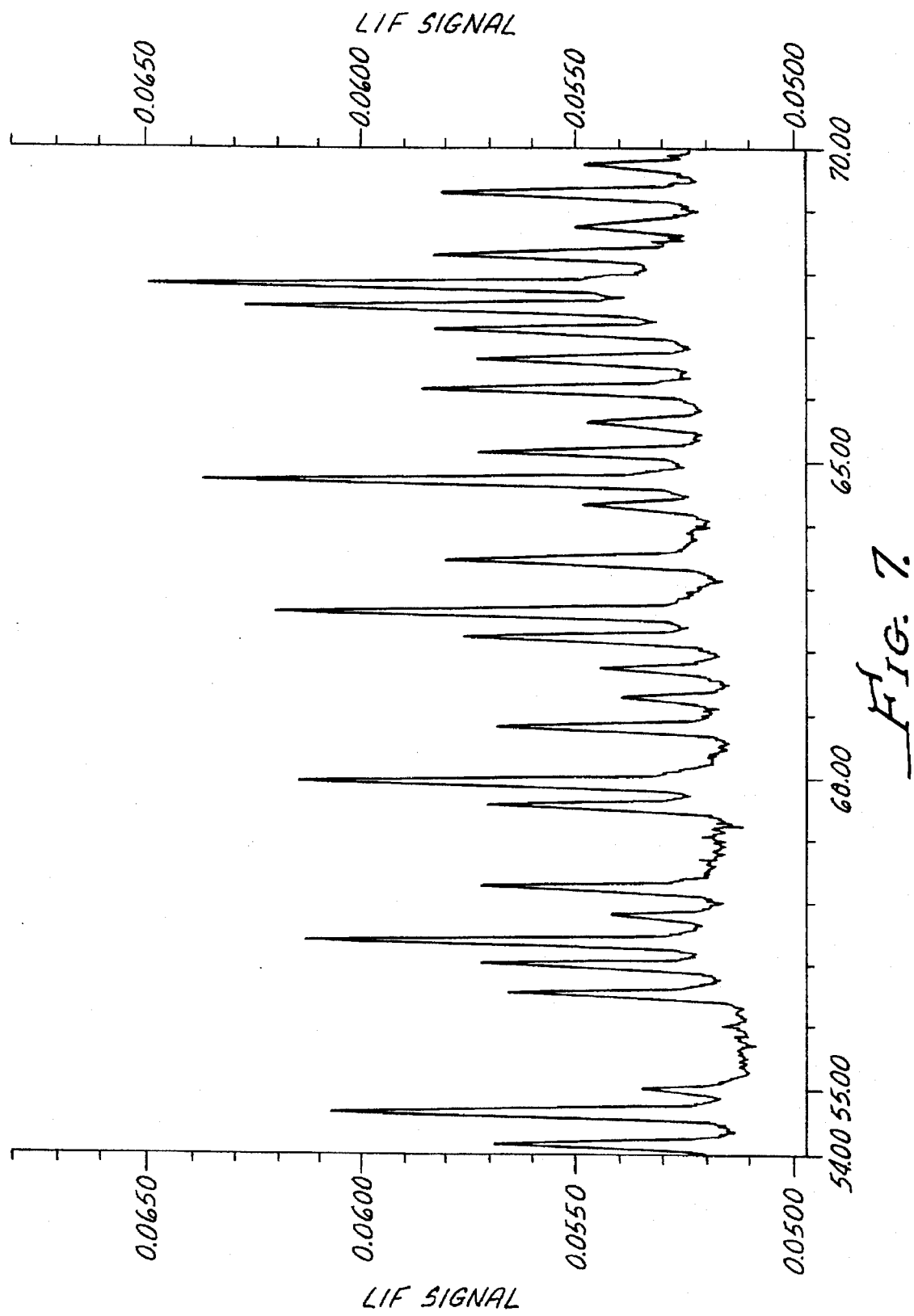
FIG. 7 is an electropherogram illustrating the result obtained using a gel-filled capillary with the conductive tip of this invention.

FIG. 2 is a side view of a capillary 12 with a metallized tip 12a to illustrate the preferred embodiment of the invention. One end 12a of the capillary includes an electrically conductive layer or coating 13. Layer or coating 13 may be formed by means of painting a metallic paint solution or vapor deposition of a metal such as aluminum or a noble metal such as gold onto the outside surface of the capillary at end 12a so that, as long as there is some moisture or other liquid electrolyte at the tip of end 12a of the capillary, layer or coating 13 is electrically connected to the electrolyte inside capillary 12. Layer or coating 13 may be electrically connected to a high voltage source HV (not shown) by a conventional means, such as an alligator clip (not shown) clipped onto the coating or layer 13. The polyimide coating or cladding of capillary 12 has been removed in region 12c to allow detection of the separated sample components, such as by means of laser induced fluorescence of tagged samples. An injection process using the capillary 12 will now be described in reference to FIGS. 3 and 4 below. Also as described below, it may be advantageous for both the inlet end 12a and the outlet end 12b to comprise electrically conductive layers, as shown in FIG. 2.

FIG. 3 is a schematic view of an electrophoretic system to illustrate the preferred embodiment of the invention. In the electrophoretic separation system 10 of FIG. 3, the sample is introduced into the inlet end 12a of the capillary 12 and a high voltage is applied by means of voltage supply 20 across the ends 12a and 12b. Capillary 12 is filled with an electrolyte such as a liquid buffer or a gel. After a sample has been introduced into the inlet end 12a, the end 12a is submersed in an electrolyte buffer 16 and high voltage supply 20 applies an electrical potential difference between buffer 16 by means of electrode 22 and end 12b of the capillary in a manner described below. The electric field present in the capillary then causes the sample introduced to separate into its components that are detected by a detector (not shown) at location 12c.

FIG. 4 is a partly cross-sectional and partly side view of a vial containing a sample and of a section of the capillary of FIGS. 2 and 3 to illustrate the preferred embodiment of the invention when used for sample injection. In reference to FIGS. 3 and 4, in order to introduce a plug of sample 14 into the inlet 12a of the capillary, end 12a is submersed into the sample solution 14 contained in the container or vial 17. The high voltage terminal 22 connected to voltage supply 20 by means of lead 26 is electrically connected to the electrically conductive layer or coating 13, such as by an alligator clip (not shown). Layer 13 is therefore brought into contact with the sample solution 14 by submersing end 12a in sample solution 14 as illustrated in FIG. 4. The electrical potential applied by source 20 between ends 12a, 12b cause an electric field to be present in the capillary, including the capillary at end 12a. Electric field present at end 12a then causes a plug of sample to be drawn into end 12a. As shown in FIG. 4, since the layer or coating 13 is attached to and becomes an integral part of the inlet end of the capillary 12, both the inlet end of the capillary and the electrical terminal 13 will be at the same location with respect to sample 14 so that the problems of misalignment between the terminal and the inlet end of the capillary illustrated in FIGS. 1B, 1C will be avoided altogether.

After a plug of sample has been electrokinetically introduced as described above, inlet end 12a is then removed from sample solution 14 in vial 17 and submersed into buffer 16 as shown in FIG. 3 so that the electrical potential applied between ends 12a, 12b by voltage supply 20 will cause electrophoretic separation of the sample in capillary 12 and detected as described above. The above-described method for sample injection can advantageously be used with very small amounts of sample, such as when the sample available is less than about 5 microliters in volume.

As shown in FIGS. 2 and 3, end 12b of the capillary may have a similar construction as end 12a; in other words, end 12b of the capillary also includes an electrically conductive terminal attached to the outlet end to permit the ground connection of the voltage supply 20 through lead 28 which may again be electrically connected to layer 13 at end 12b by means of an alligator clip (not shown). If the capillary surface is charged, the electrical potential applied by voltage supply 20 across the ends of the capillary will cause electroosmotic flow so that the liquid effluent coming out of end 12b of the capillary will electrically connect layer 13 at end 12b to the liquid buffer inside the capillary so as to complete the circuit between the voltage supply 20 and the capillary. When capillary 12 contains a gel electrolyte and collection of undiluted separated components is desired, it is preferable to maintain the electrical contact between the gel medium inside the capillary and layer 13 at end 12b by means of a collection device with a preferably continuous surface such as a wet membrane in the configuration shown in FIG. 5. As shown in FIG. 5, the effluent from end 12b is deposited onto a wet membrane 60 moving in direction 62. In this manner, the separated components of a sample emerging from end 12b will be deposited onto membrane 60 so that the separated component would not be mixed with a different component deposited onto a different portion of the membrane 60. Obviously, instead of moving surface 60 along arrow 62, it is also possible to keep surface 60 stationary and move end 12b of the capillary in a direction opposite the direction 62; it is possible also to cause relative motion between the end 12b and surface 60 by moving both surface 60 and end 12b to accomplish similar results.

Instead of depositing the separated components in the effluent from end 12b onto a surface 60, it is also possible to deposit each separated component into a small amount of buffer solution such as solution 70 contained in vial 17 as shown in FIG. 6. In this manner, the separated component would not be unduly diluted since the component is deposited into a very small amount of fluid 70.

Instead of completing the circuit as described above using an electrically conductive outlet end 12b, it is possible to complete the circuit using a conventional buffer solution such as buffer 80 (see FIG. 3) where an electrically conductive or non-conductive end 12b' of capillary 12 is submersed as shown partly in phantom in FIG. 2. Submersed also is an electrode 24 connected to the ground terminal of voltage supply 20 by means of lead 28.

In the fabrication of one embodiment of the invention, one of the tips (approximately 180° around, and two inches in length) was coated with an electrically conductive layer by vapor deposition of aluminum. The capillary column is then coated with a layer for eliminating surface charge and filled with a gel. The capillary column was pre-conditioned at 5 and 10 kV for one hour prior to an electrophoresis process. A portion of an electropherogram resulting from the run is shown in FIG. 7.

While the invention has been described above in reference to various embodiments, it will be understood that various changes and modifications may be made without departing from the scope of the invention which is to be limited only by the appended claims.

What is claimed is:

1. An apparatus for electrokinetic injection of a sample, comprising:

a capillary tube having an end submersed in a sample;

an electrically conductive terminal attached to the tube at said end;

means electrically connected to said terminal for applying an electric field at said end of the tube, so that when said end is submersed in a sample, that will cause a portion of said sample to be introduced into the submersed end of the tube.

2. The apparatus of claim 1, further comprising means for collecting and maintaining separated components of said sample in a separated state.

3. The apparatus of claim 2, wherein the collecting and maintaining means comprises:

a collection means positioned in flow communication with the exit of the capillary tube; and means for distributing the separated components spatially on the collection means.

4. The apparatus of claim 3 wherein the collection means is a continuous surface.

5. The apparatus of claim 2, wherein the means for distributing causes relative motion between the collection means and the exit of the capillary tube such that the separated components are distributed and remain separated.

6. The apparatus of claim 1, further comprising a liquid electrolyte in the tube.

7. The apparatus of claim 1, further comprising a gel electrolyte in the tube.

8. The apparatus of claim 1, said terminal attached to the tube at said inlet end comprising a metal coating on said inlet end.

* * * * *